(12) United States Patent
He

(10) Patent No.: US 7,840,279 B2
(45) Date of Patent: Nov. 23, 2010

(54) IMPLANTABLE MICROSTIMULATOR HAVING A SEPARATE BATTERY UNIT AND METHODS OF USE THEREOF

(75) Inventor: Tom Xiaohai He, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 504 days.

(21) Appl. No.: 11/056,762

(22) Filed: Feb. 11, 2005

(65) Prior Publication Data

US 2006/0184204 A1    Aug. 17, 2006

(51) Int. Cl.
*A61N 1/05* (2006.01)
(52) U.S. Cl. .................. 607/116; 607/55; 607/56; 607/57; 607/61; 607/118
(58) Field of Classification Search .......... 607/2, 607/61, 116, 118, 55–57
See application file for complete search history.

(56) References Cited

U.S. PATENT DOCUMENTS

| | | |
|---|---|---|
| 3,522,811 A | 8/1970 | Schwartz et al. |
| 3,718,142 A | 2/1973 | Mulier |
| 4,143,661 A | 3/1979 | LaForge et al. |
| RE30,366 E | 8/1980 | Rasor et al. |
| 4,333,469 A | 6/1982 | Jeffcoat et al. |
| 4,379,462 A | 4/1983 | Borkan et al. |
| 4,414,979 A | 11/1983 | Hirshorn et al. |
| 4,432,377 A | 2/1984 | Dickhudt |
| 4,524,774 A | 6/1985 | Hildebrandt |
| 4,573,481 A | 3/1986 | Bullara |
| 4,612,934 A | 9/1986 | Borkan |
| 4,793,353 A | 12/1988 | Borkan |
| 4,905,285 A | 2/1990 | Allen et al. |
| 4,989,617 A | 2/1991 | Memberg et al. |
| 5,002,053 A | 3/1991 | Garcia-Rill et al. |
| 5,105,811 A | 4/1992 | Kuzma |
| 5,193,539 A | 3/1993 | Schulman et al. |
| 5,193,540 A | 3/1993 | Schulman et al. |
| 5,211,175 A | 5/1993 | Gleason et al. |
| 5,257,634 A | 11/1993 | Kroll |
| 5,282,468 A | 2/1994 | Klepinski |
| 5,312,439 A | 5/1994 | Loeb |
| 5,324,316 A | 6/1994 | Schulman et al. |
| 5,358,514 A | 10/1994 | Schulman et al. |
| 5,366,493 A | 11/1994 | Scheiner et al. |

(Continued)

FOREIGN PATENT DOCUMENTS

WO    WO 98/37926    9/1998

(Continued)

OTHER PUBLICATIONS

U.S. Appl. No. 11/040,209, filed Jan. 20, 2005 to Colvin et al.

*Primary Examiner*—Carl H Layno
*Assistant Examiner*—Deborah Malamud
(74) *Attorney, Agent, or Firm*—Frommer Lawrence & Haug LLP; Bruce E. Black

(57) ABSTRACT

An implantable microstimulator arrangement includes at least one implantable microstimulator unit; an implantable battery unit separate from the implantable microstimulator unit(s); and at least one lead coupling the microstimulator unit(s) to the battery unit. The microstimulator unit(s) are operated to treat body tissue.

22 Claims, 7 Drawing Sheets

U.S. PATENT DOCUMENTS

| | | | |
|---|---|---|---|
| 5,405,367 A | 4/1995 | Schulman et al. | |
| 5,458,629 A | 10/1995 | Baudino et al. | |
| 5,531,787 A * | 7/1996 | Lesinski et al. | 623/10 |
| 5,591,217 A | 1/1997 | Barreras | |
| 5,741,316 A | 4/1998 | Chen et al. | |
| 5,807,397 A | 9/1998 | Barreras | |
| 5,945,762 A | 8/1999 | Chen et al. | |
| 5,957,958 A | 9/1999 | Schulman et al. | |
| 5,991,664 A | 11/1999 | Seligman | |
| 6,051,017 A | 4/2000 | Loeb et al. | |
| 6,064,913 A | 5/2000 | Irlicht et al. | |
| 6,067,474 A | 5/2000 | Schulman et al. | |
| 6,078,838 A | 6/2000 | Rubinstein | |
| 6,092,531 A | 7/2000 | Chen et al. | |
| 6,154,677 A | 11/2000 | Leysieffer | |
| 6,154,678 A | 11/2000 | Lauro | |
| 6,185,452 B1 | 2/2001 | Schulman et al. | |
| 6,198,971 B1 | 3/2001 | Leysieffer | |
| 6,216,045 B1 | 4/2001 | Black et al. | |
| 6,219,580 B1 | 4/2001 | Faltys et al. | |
| 6,246,911 B1 | 6/2001 | Seligman | |
| 6,272,382 B1 | 8/2001 | Faltys et al. | |
| 6,289,247 B1 | 9/2001 | Faltys et al. | |
| 6,358,281 B1 | 3/2002 | Berrang et al. | |
| 6,464,687 B1 | 10/2002 | Ishikawa et al. | |
| 6,542,777 B1 | 4/2003 | Griffith et al. | |
| 6,609,032 B1 | 8/2003 | Woods | |
| 6,700,982 B1 | 3/2004 | Geurts et al. | |
| 7,069,075 B2 * | 6/2006 | Olson | 607/5 |
| 2003/0004546 A1 * | 1/2003 | Casey | 607/1 |
| 2003/0114905 A1 | 6/2003 | Kuzma | |
| 2004/0059392 A1 | 3/2004 | Parramon et al. | |
| 2005/0004619 A1 * | 1/2005 | Wahlstrand et al. | 607/45 |
| 2006/0161204 A1 | 7/2006 | Colvin et al. | |

FOREIGN PATENT DOCUMENTS

| | | |
|---|---|---|
| WO | WO 98/43700 | 10/1998 |
| WO | WO 98/43701 | 10/1998 |

* cited by examiner

IMPLANTABLE MICROSTIMULATOR HAVING A SEPARATE BATTERY UNIT AND METHODS OF USE THEREOF

FIELD

The invention is directed to implantable microstimulator arrangements having a separate implantable battery unit and methods of using the microstimulator arrangements.

BACKGROUND

Implantable microstimulators have been developed to provide therapy for a variety of disorders, as well as other treatments. For example, implantable microstimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Implantable microstimulators, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissue. It is often preferable that the microstimulator be as small as possible to provide stimulation to the desired tissue without substantially disturbing surrounding tissue. Therefore, the battery for the microstimulator is typically small and often rechargeable. In many instances, the battery must be recharged every day or several days, at least in part because of its small size.

BRIEF SUMMARY

One embodiment is an implantable microstimulator arrangement that includes at least one implantable microstimulator unit; an implantable battery unit separate from the implantable microstimulator unit(s); and at least one lead coupling the microstimulator unit(s) to the battery unit.

Another embodiment is an implantable microstimulator arrangement that includes at least one implantable battery unit; a plurality of implantable microstimulator units; a plurality of lead connectors; and a plurality of leads that couple the microstimulator units to the battery unit(s) using the lead connectors.

Yet another embodiment is a method of treating body tissue. The method includes implanting at least one microstimulator unit into a body in the proximity of the body tissue to be treated. A separate battery unit is also implanted into the body and the battery unit is coupled to the microstimulator unit(s) using at least one lead. The microstimulator unit(s) are then operated to treat the body tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable microstimulators and methods of using the microstimulators. An implantable microstimulator can include a separate implantable battery unit that is coupled to one or more implantable microstimulator units by a lead or a number of leads and lead connectors.

Previously, implantable microstimulators have been made with batteries disposed in the housing of the microstimulator. Examples of such microstimulators are found in U.S. Pat. Nos. 5,193,539; 5,193,540; 5,312,439; 6,051,017; and 6,609,032; U.S. Patent Application Publication No. 2004/059392; PCT Patent Applications Publication Nos. 98/37926; 98/43700; and 98/43701; and U.S. patent application Ser. No. 11/040,209, entitled "Implantable microstimulator with plastic housing and methods of manufacture and use," filed on Jan. 20, 2005, all of which are incorporated herein by reference.

Figure 1:
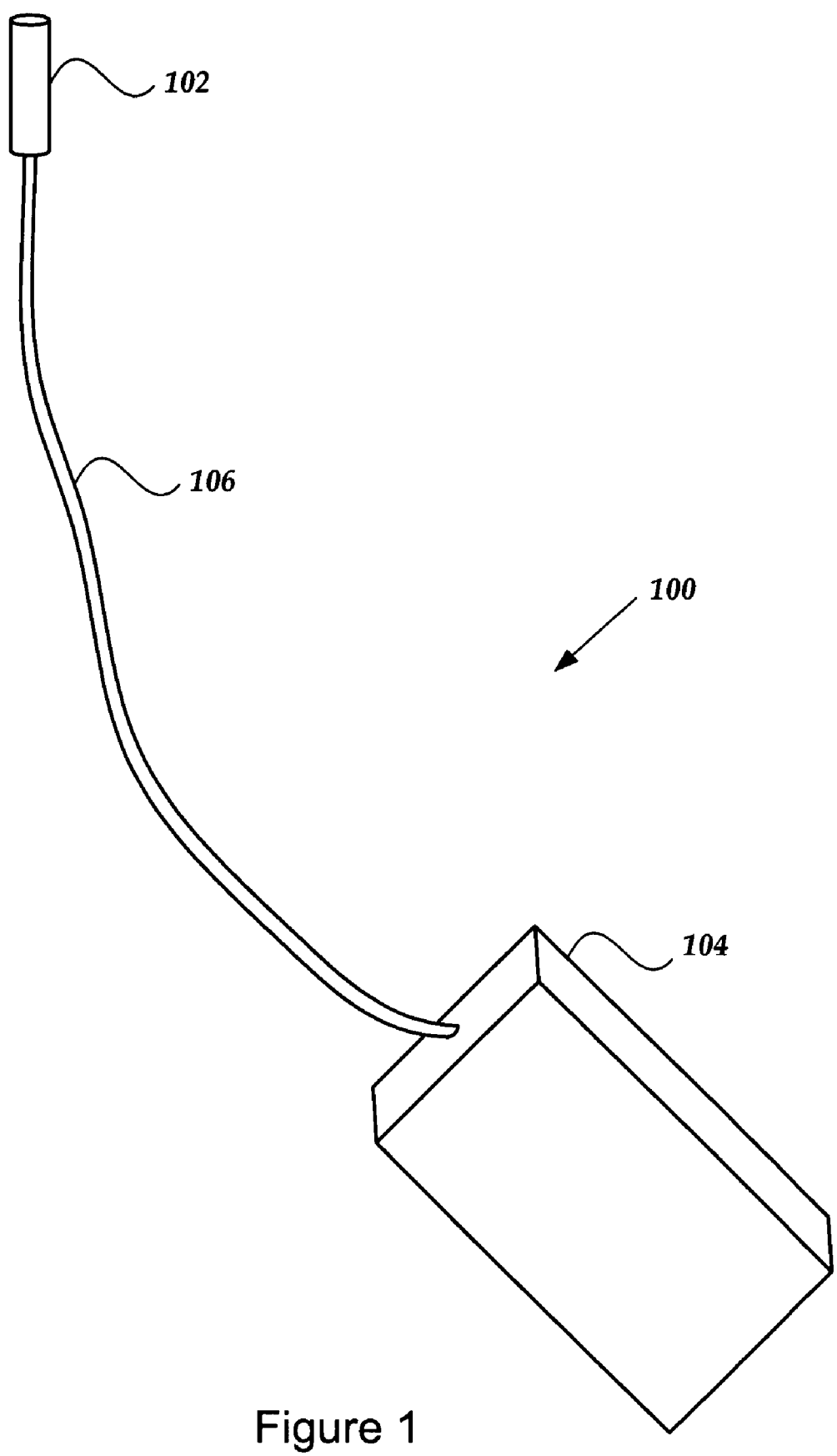
FIG. 1 is a schematic perspective view of one embodiment of a microstimulator arrangement, according to the invention.

FIG. 1 illustrates one embodiment of a microstimulator arrangement 100 that includes an implantable microstimulator unit 102, an implantable battery unit 104, and a lead 106 extending between the microstimulator unit and the battery unit. Both the microstimulator unit 102 and the battery unit 104 are implantable. The microstimulator unit 102 can be implanted in contact with or near the tissue to be stimulated. The battery unit 104 can be implanted in a position, for example, near the skin, that is more accessible for charging or replacement, from which it is easier to remove the battery unit, if desired, or which is more comfortable for the patient.

Figure 2:
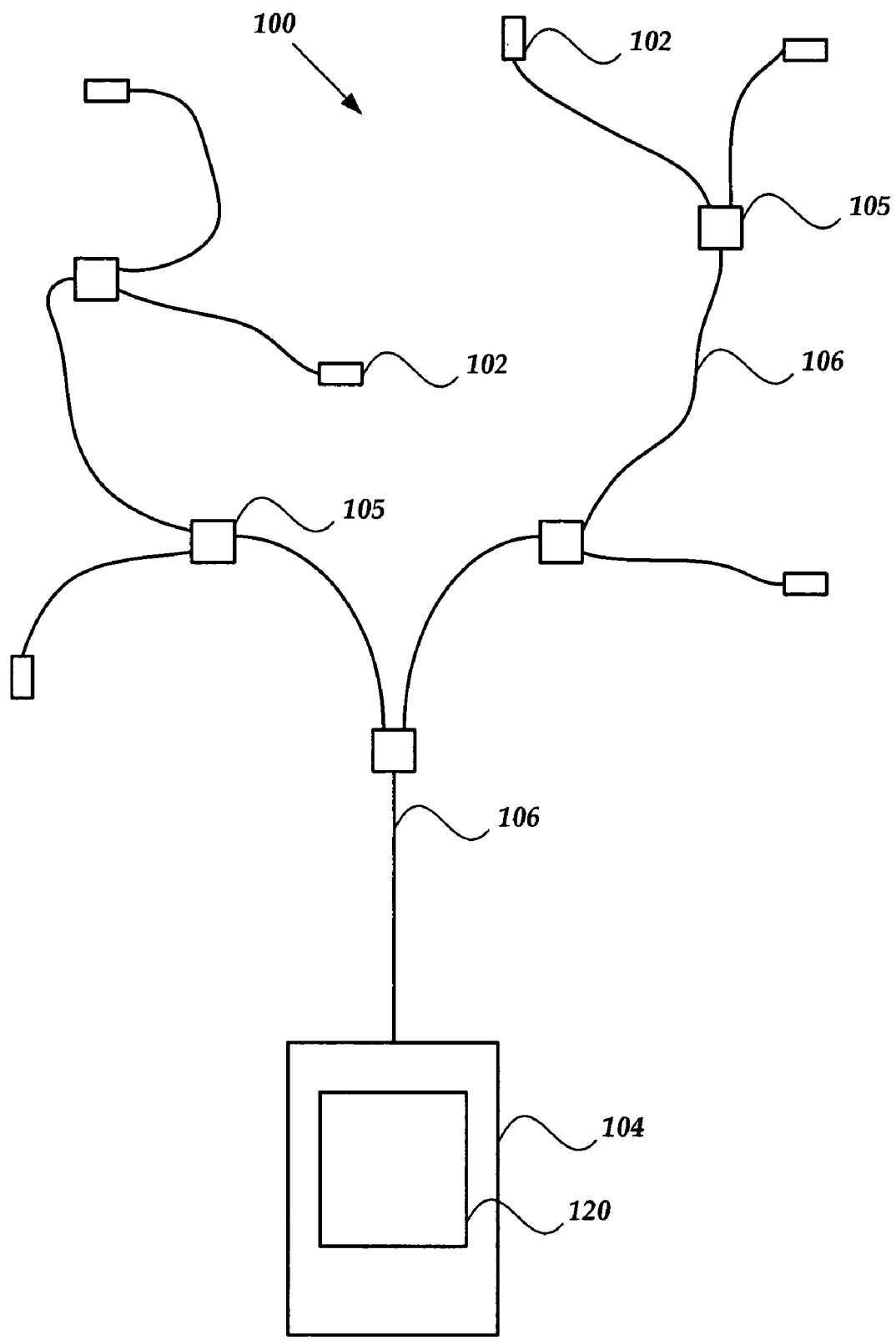
FIG. 2 is a schematic plan view of another embodiment of a microstimulator arrangement according to the invention.

FIG. 2 illustrates a microstimulator arrangement 100 with a single battery unit 104 and multiple microstimulator units 102 connected to the battery unit by multiple leads 106 and lead connectors 105. It will be recognized that any number of microstimulators units 102 can be used and that any number of leads 106 can be coupled to a lead connector 105. Furthermore, it will be recognized that the microstimulator arrangement can include more than one battery unit. Each of the individual microstimulator units can be implanted anywhere in the body of the patient. The microstimulator units can be used to stimulate the same tissue or different tissue regions.

The battery unit will typically include at least a housing and a power source. Any power source can be used in the battery unit 104. For example, the battery unit can contain at least one battery such as a primary battery or a rechargeable battery. Examples of other power sources for the battery unit include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

If the power source 120 of the battery unit 104 is a rechargeable battery or other rechargeable power source, the battery may be recharged using an optional antenna 124 (see FIGS. 3 and 4), if desired. The optional antenna 124 is disposed in or on the housing of the battery unit 104. Power can be provided to the rechargeable power source for recharging by inductively coupling the rechargeable power source through the antenna 124 to a recharging unit 210 (see FIGS. 3 and 4) external to the patient.

Figure 3:
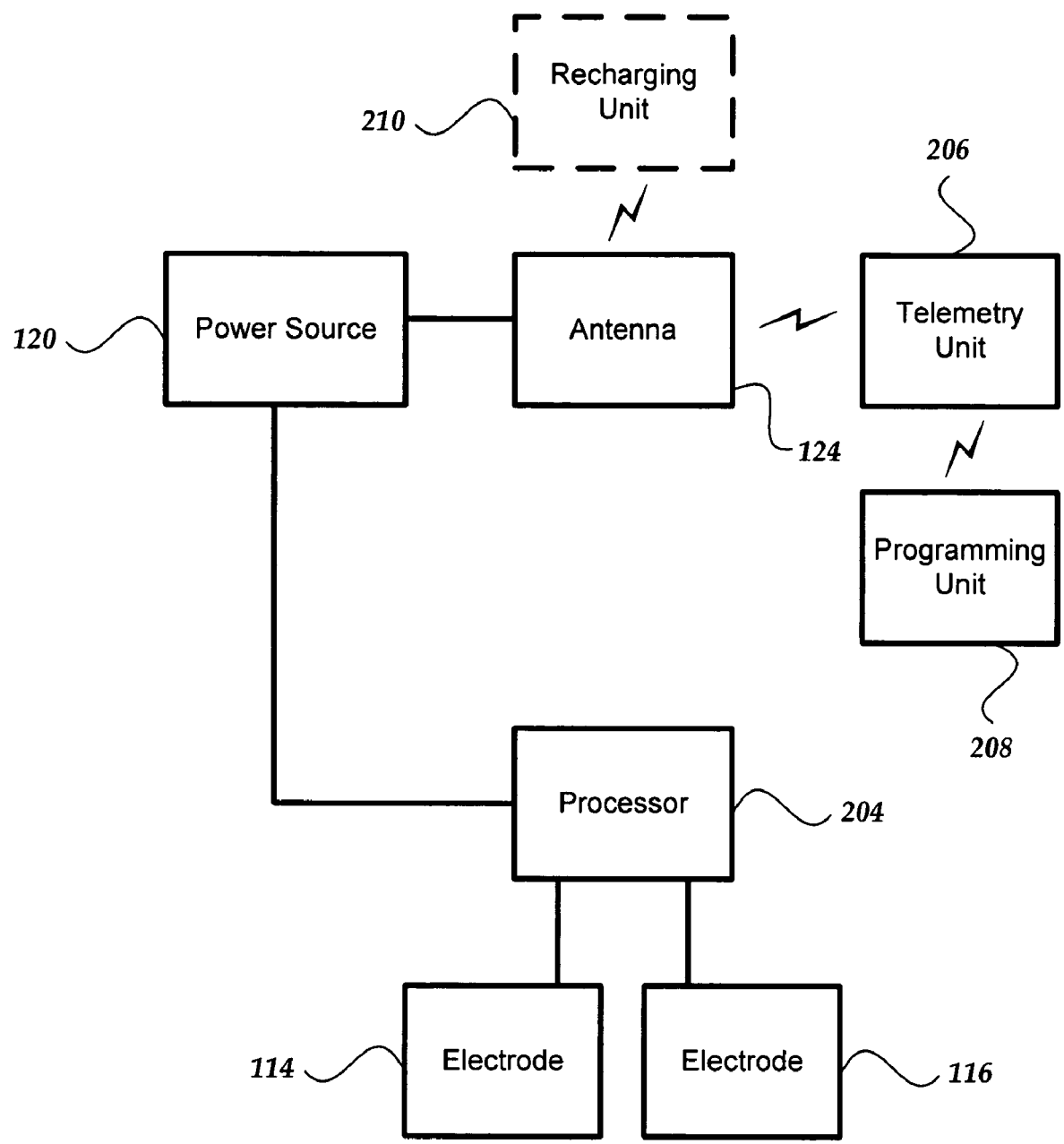
FIG. 3 is a schematic overview of one embodiment of components for a system for microstimulation of body tissues, according to the invention.

Communication and/or control signals for the microstimulator arrangement are optionally transmitted via the antenna 124 to the battery unit (as illustrated in FIG. 3) and can be carried to the microstimulator unit 102 by modulating the electrical power supplied by the battery unit 104. The battery unit 104 can also optionally include electronic circuitry, such as a DC/AC converter or a portion of the electronic subassembly, described below, for the operation of the microstimulator unit. Electrical power delivered from the battery unit 104 to the microstimulator unit 102 can be DC power or it may be converted from DC to AC in the battery unit and the AC may then be delivered via a connecting lead structure and to the microstimulator or microstimulators.

Figure 4:
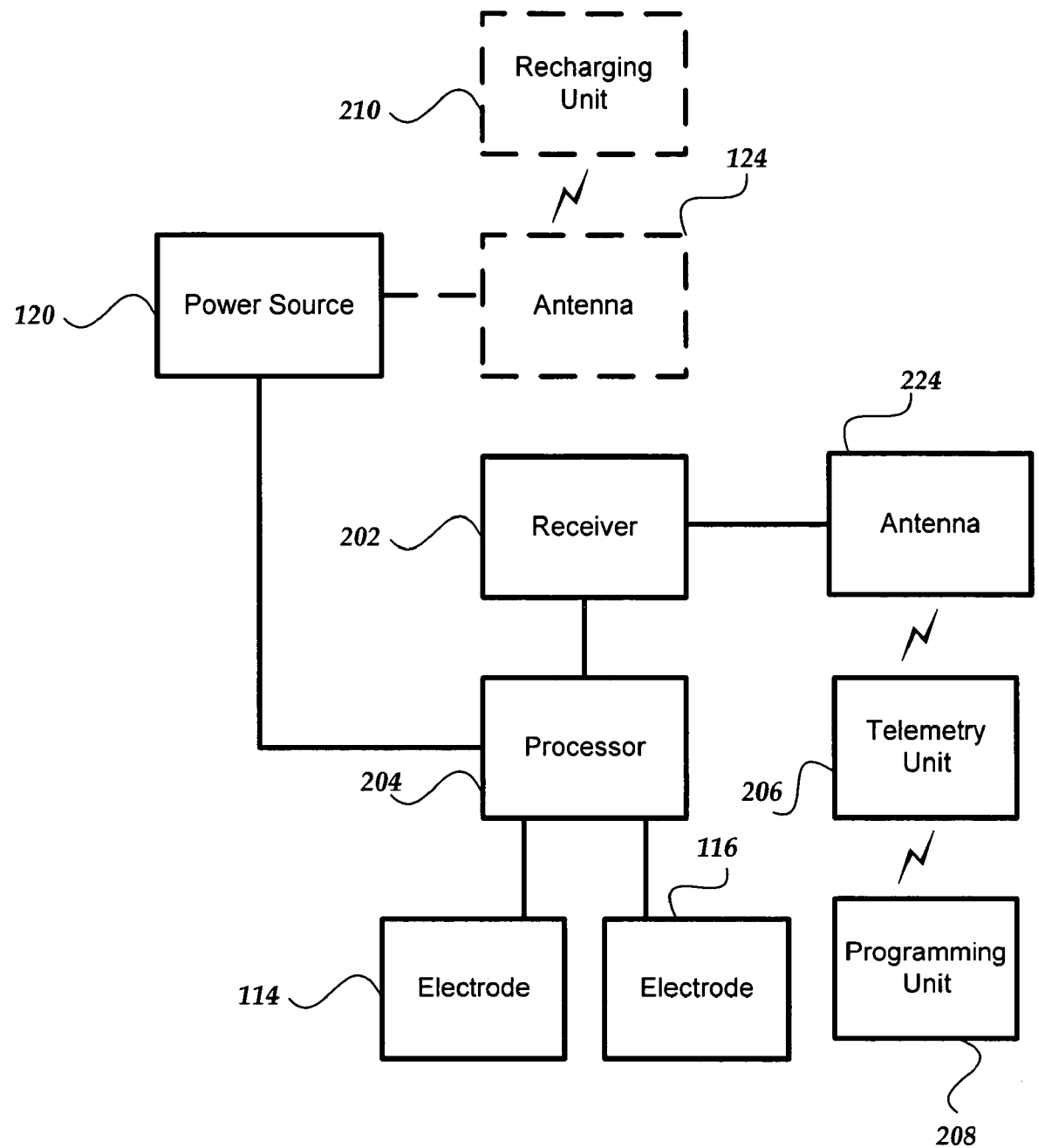
FIG. 4 is a schematic overview of another embodiment of components for a system for microstimulation of body tissues, according to the invention.
Figure 5:
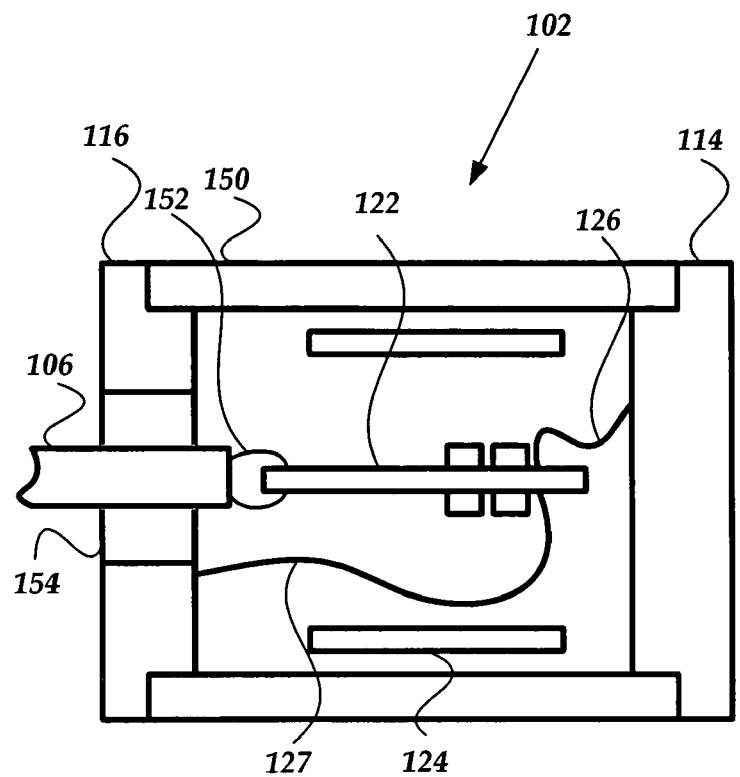
FIG. 5 is a schematic cross-sectional view of one embodiment of a microstimulator unit, according to the invention.
Figure 6:
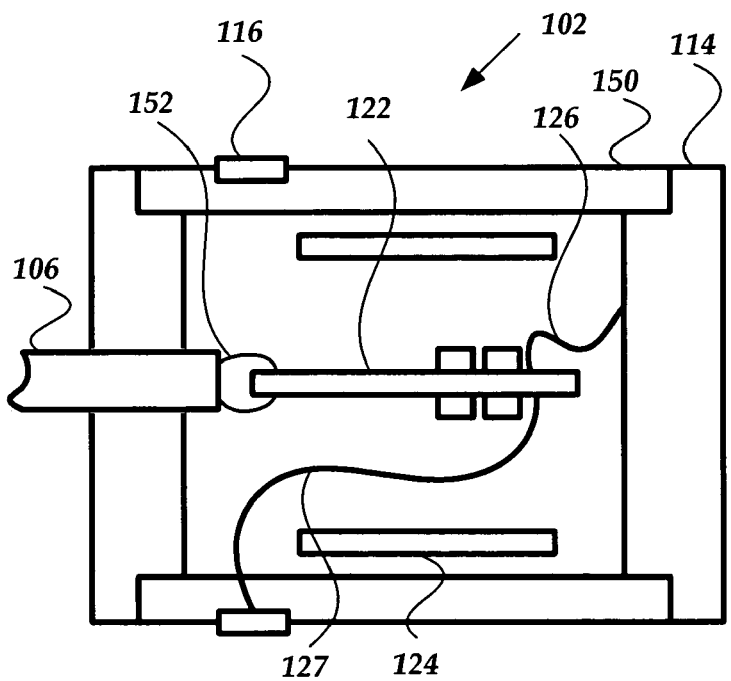
FIG. 6 is a schematic cross-sectional view of another embodiment of a microstimulator unit, according to the invention.
Figure 7:
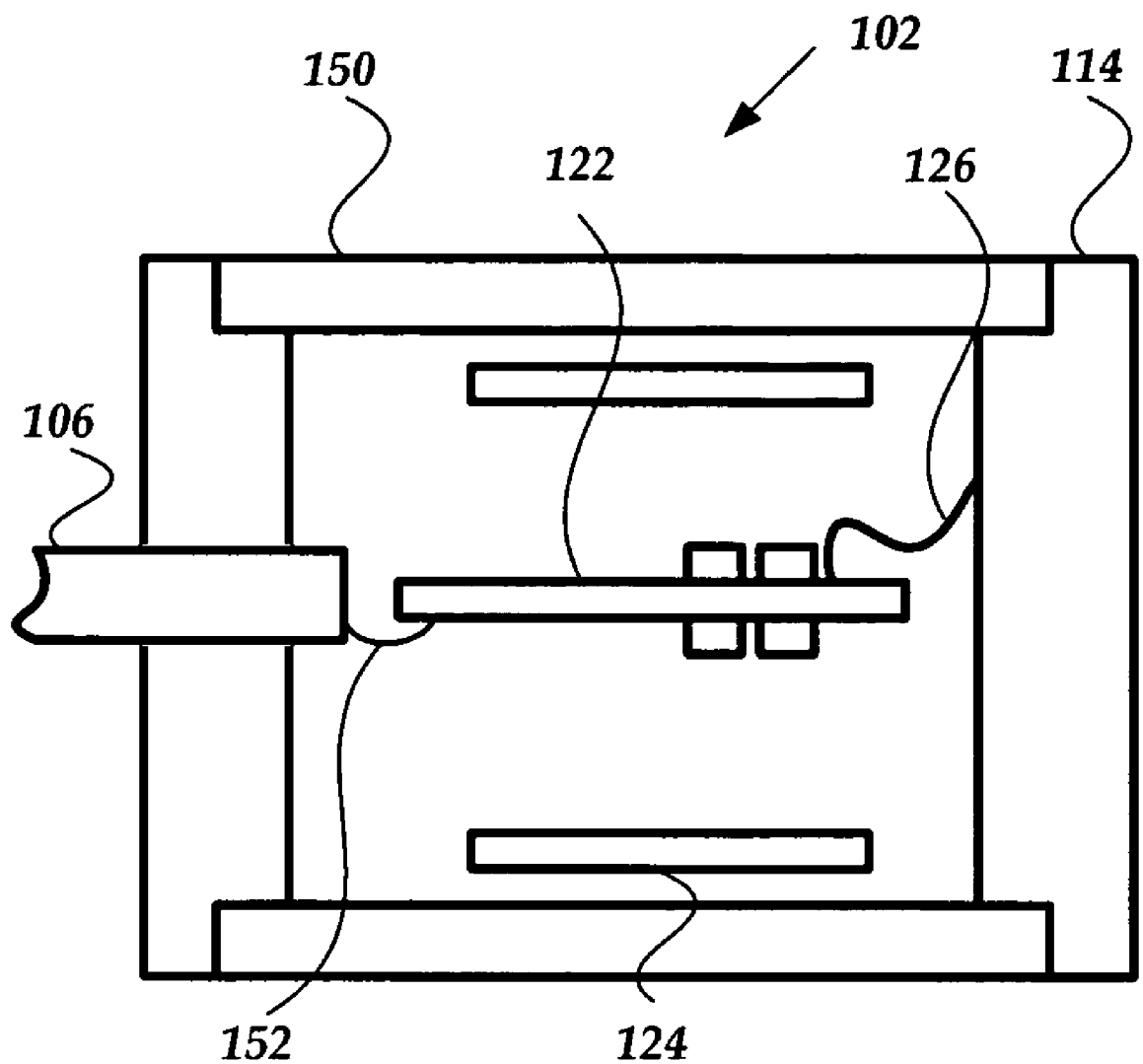
FIG. 7 is a schematic cross-sectional view of a third embodiment of a microstimulator unit, according to the invention.

Schematic examples of suitable microstimulator units are illustrated in FIGS. 5, 6, and 7. It will be understood that a variety of other microstimulator unit configurations can be used. The microstimulator unit 102 typically includes a housing 150, one or more electrodes (for example, electrodes 114, 116), and an electronic subassembly 122. When the microstimulator unit includes only one electrode (see, for example, FIG. 7), the second, indifferent, electrode can be associated with the battery unit 104, lead 106, or lead connector 105; for example, the second, indifferent, electrode can be the case of the battery unit or lead connector. Electrical current is emitted by one or more electrodes (for example, the two electrodes 114, 116 of FIGS. 4, 5) to stimulate tissue such as, for example, motor nerve fibers, muscle fibers, or other body tissues near the microstimulator unit.

The housing 150 of the microstimulator unit 102 can be formed of any material that resists the transport of moisture into the interior of the housing and is sufficiently sturdy to protect the components on the interior of the housing from damage under expected implantation and usage conditions. Examples of such materials include metals, alloys, ceramics, and plastics. Examples of microstimulator units with plastic housings are disclosed in U.S. patent application Ser. No. 11/040,209, entitled "Implantable microstimulator with plastic housing and methods of manufacture and use," filed on Jan. 20, 2005, incorporated herein by reference. In at least some embodiments, the housing 150 is formed using two or more different materials that are joined together. For example, a portion of the housing can be made of a metal or alloy and a second portion of the housing can be made of ceramic. These portions can be joined together by, for example, brazing.

The housing 150 can have any shape including, for example, cylindrical, conical, parallelepiped, cubic, and the like. In at least some embodiments, a cylindrical shape is preferred. The lateral cross-sectional dimensions can be the same or can vary along the length of housing. In one embodiment, the housing has a cylindrical shape with a uniform diameter along the length of the housing. The uniform diameter can be, for example, up to 8 mm in diameter and, more preferably, the uniform diameter may range between about 1 to 5 mm in diameter. In another embodiment, the housing is a cylinder that is wider at the ends and narrower in the middle or the housing is a cylinder that is wider in the middle and narrower at the ends.

Optionally, the housing can be covered, in full or in part, with a coating. The coating can be provided to improve or alter one or more properties of the housing including, for example, biocompatibility, hydrophobicity, moisture permeability, leaching of material into or out of the housing, and the like. The optional coating can be a polymer material, inorganic material, or organic material. As an example, the housing may be coated with an inorganic material, such as, for example, silicon dioxide, silicon nitride, titanium dioxide, or the like, to reduce moisture permeability. As another example, a silicone coating may be used to cover the housing to improve biocompatibility. In yet another example, a coating can be applied which contains a compound, such as, for example, a drug, prodrug, hormone, or other bioactive molecule, that can be released over time when the microstimulator is implanted. (In another embodiment, a plastic housing itself may include such a compound to be released over time after implantation.) In some embodiments, the coating includes two or more layers of the same or different materials. For example, alternating layers of inorganic materials can be deposited as a coating to improve resistance to moisture transport through the housing.

The formation of the coating can be accomplished using any method including, for example, dip-coating, sputtering, reactive sputtering, physical or chemical vapor deposition, spray coating, and the like. The coating can be applied before the other microstimulator components have been assembled within the housing or at any other point in the microstimulator manufacturing process including applying the coating after the microstimulator has been completely assembled. Typically, the coating is non-conductive.

The one or more electrodes 114, 116 of the microstimulator unit can be formed using any conductive material including metals and alloys. Preferably, the electrodes are formed of material(s) that does not substantially corrode under the operating conditions and in the operating environment for the expected lifetime of the microstimulator unit. Examples of suitable materials include conductive materials such as, for example, titanium, iridium, platinum, platinum/iridium alloy, stainless steel, and the like.

The electrodes 114, 116 can be formed entirely of a single conductive material, such as a metal or alloy, or one or both of the electrodes can be formed using a combination of conductive materials such as, for example, a conductive coating over a bulk metallic electrode. As another example, one or both of the electrodes 114, 116 can be formed from a polymeric material that is at least partially, or fully, coated with a conductive coating, such as a metal, alloy, or conductive oxide (e.g., iridium oxide) coating.

In one embodiment, each of the one or more electrodes is a solid body that fits into one end of the housing 150, as illustrated for example in FIG. 5. The electrode can be coupled to the battery and electronic subassembly by attaching a conductor 126, 127 to a surface of the electrode. As an alternative, one or both of the electrodes 114 or 116 can include a hole through the electrode body. A conductor from the electronic subassembly 122 or power source 120 can then be guided through the hole and the lead can be attached to a conductive exterior surface of the electrode. The attachment of the lead to the electrode can be performed by any method including, for example, soldering or laser welding. Generally, if a hole through the electrode body is utilized, the hole is also sealed prior to, simultaneously with, or after the attachment of the lead to the electrode surface to maintain a hermetically-sealed environment within the housing. Other methods and arrangements for attaching a lead to each electrode can be used.

In one embodiment, one or both of the electrodes 114, 116 may be positioned at ends of the housing 150 as illustrated, for example, in FIGS. 5, 6, and 7. In at least some embodiments, the electrodes 114, 116 are disposed at opposing or opposite ends of the housing 150. For example, the electrodes 114, 116 can be disposed at opposite ends of a cylindrical housing, as illustrated in FIG. 5.

One of the electrodes (e.g., electrode 116 of FIG. 5), or a portion of the housing as illustrated in FIGS. 6 and 7, defines an opening through which lead 106 can pass. Preferably, this opening is hermetically sealed for implantation and operation of the microstimulator arrangement. Optionally, as illustrated in FIG. 5 a non-conductive region 154 can be formed around this opening to prevent or resist conduction of electricity between the electrode 116 and the lead 106. In other embodiments, the sheathing about the lead is sufficient to prevent or resist conduction of electricity.

In some embodiments, one or both of the electrodes 114, 116 can be formed around the circumference of the housing. One example of such an arrangement is illustrated in FIG. 6. In this example, the electrode 114 forms a ring around the housing 150. The electrode 114 can be partially or fully embedded in the housing 150 or the electrode 114 can be formed over the housing 150.

The electronic subassembly 122 provides the electronics used to operate the microstimulator and generate the electrical pulses at the electrodes 114, 116 to produce stimulation of the body tissues. FIGS. 3 and 4 illustrate two embodiments with components of the electronic subassembly and associated units. It will be understood that the electronic subassembly can include more, fewer, or different components and can have a variety of different configurations including those configurations disclosed in the microstimulator references cited above. Some or all of the components of the electronic subassembly can be positioned on one or more circuit boards or similar carriers within the housing, if desired. Some or all of the components of the electronic subassembly can be disposed in the microstimulator unit or portions of the electronic subassembly (e.g., the processor 204) can be disposed in the battery unit.

In the illustrated embodiments, a processor 204 is provided to control the timing and electrical characteristics of the microstimulator. For example, the processor can, if desired, control one or more of the timing, periodicity, strength, duration, and waveform of the electrical pulses provided at the electrodes. Any processor can be used and the processor can be as simple as a electronic device that produces pulses at a regular interval or the processor can be capable of receiving and interpreting instructions from an external programming unit 208 that allow modification of pulse characteristics.

In the illustrated embodiment of FIG. 3, the processor receives signals via the power source 120. In this embodiment, a programming unit 208 is used to determine what signals should be provided to the microstimulator arrangement 100. The programming unit 208 sends signals to a telemetry unit 206 which then broadcasts signals to the power source 120 via the optional antenna 124. The power source can, for example, overlay these signals on the power provided to the microstimulator unit 102.

In another embodiment illustrated, for example, in FIG. 4, the processor 204 is coupled to a receiver 202 which, in turn, is coupled to an antenna 224. This allows the processor to receive instructions from an external source, such as the telemetry unit 206 and programming unit 208, to direct the pulse characteristics. In at least some embodiments, when multiple microstimulator units are provided, the receivers 202 of the microstimulator units can be tuned to different frequencies or each microstimulator unit may be identified by a unique identifier that is transmitted by the telemetry unit to indicate which microstimulator unit is addressed.

In these illustrated embodiments, the antenna 124 or 224 is capable of receiving signals (e.g., infrared or RF signals) from an external telemetry unit 206 which is programmed by a programming unit 208. The programming unit 208 can be external to, or part of, the telemetry unit 206. The telemetry unit 206 can be, for example, a device that is worn on the skin of the patient, or can be carried by the patient and can have a form similar to a pager or cellular phone, if desired. As another alternative, the telemetry unit may not be worn or carried by the patient but may only be available at a home station or at a clinician's office. The programming unit 208 can be any unit that can provide information to the telemetry unit for transmission to the implanted microstimulator. The programming unit 208 can be part of the telemetry unit 206 or can provide signals or information to the telemetry unit via a wireless or wired connection. One example of a suitable programming unit is a computer operated by the patient or clinician to send signals to the telemetry unit.

The signals sent to the processor 204 can be used to modify or otherwise direct the operation of the microstimulator. For example, the signals may be used to modify the pulses of the microstimulator such as modifying one or more of pulse duration, pulse frequency, pulse waveform, and pulse strength. The signals may also direct the microstimulator to cease operation or to start operation or to start charging the battery.

Optionally, the microstimulator unit or battery unit (or both) can include a transmitter (not shown) coupled to the processor and antenna for transmitting signals back to the telemetry unit 206 or another unit capable of receiving the signals. For example, the microstimulator may transmit signals indicating whether the microstimulator is operating properly or not or indicating when the battery needs to be charged. The processor may also be capable of transmitting information about the pulse characteristics so that a patient or clinician can determine or verify the characteristics.

The optional antennas 124, 224 can have any form. In one embodiment, the antenna 124 comprises a coiled wire that is wrapped at least partially around the power source in the battery unit 104. In another embodiment, the antenna 224 comprises a coiled wire that is wrapped at least partially around the electronic subassembly within the housing, as illustrated, for example, in FIGS. 5, 6, and 7.

Any method of manufacture of the microstimulator unit can be used. For example, the electronic subassembly and antenna can be manufactured in a manner similar to that described in U.S. Patent Application Publication No. 2004/0059392. These components can then be placed inside the housing (or, alternatively, the housing can be formed, e.g., molded, around the components). The electrodes can be attached to the housing, for example, screwed into opposite ends of the housing, and leads from the electronic subassembly can be attached to the electrodes. Coatings on the electrodes or housing, if any, can be applied at appropriate points during the manufacturing process.

Each lead 106 of the microstimulator arrangement 100 includes one or more conductors disposed within a non-conductive, biocompatible sheathing. A lead can be removably or non-removably coupled or couplable to a microstimulator unit 102, battery unit 104, or lead connector 105. FIG. 1 illustrates one embodiment in which the lead 106 is non-removably coupled to a microstimulator unit 102 and a battery unit 104. In other embodiments, one end of the lead 106 can be non-removably coupled to a microstimulator unit 102, battery unit 104, or lead connector 105 and the other end of the lead 106 can be removably coupled or couplable to a microstimulator unit 102, battery unit 104, or lead connector 105. In yet other embodiments, both ends of the lead 106 are removably coupled or removably couplable.

Figure 8:
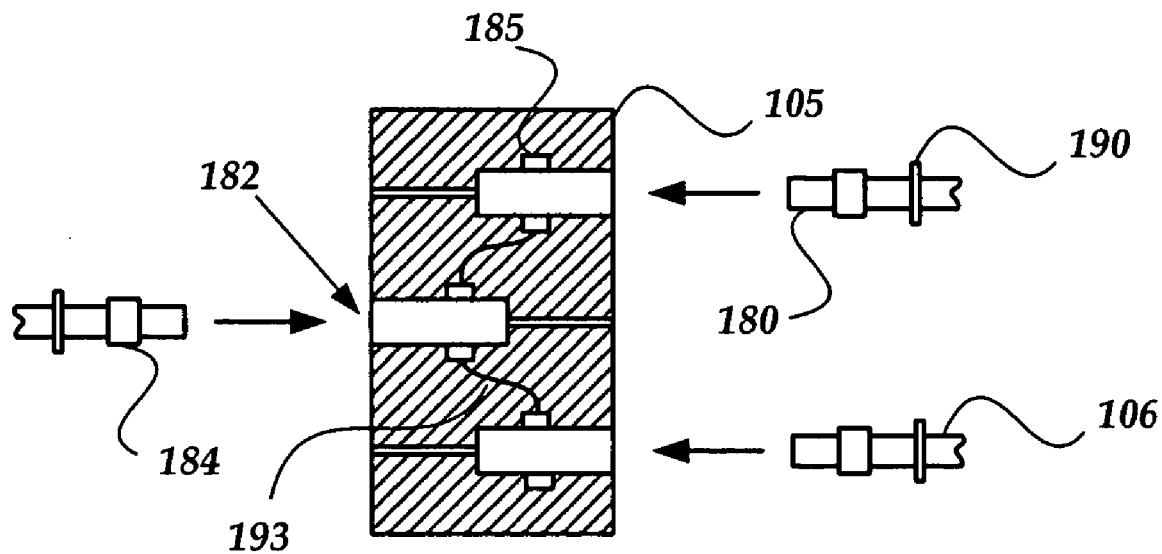
FIG. 8 is a schematic cross-sectional view of one embodiment of a lead connector and leads, according to the invention.
Figure 9:
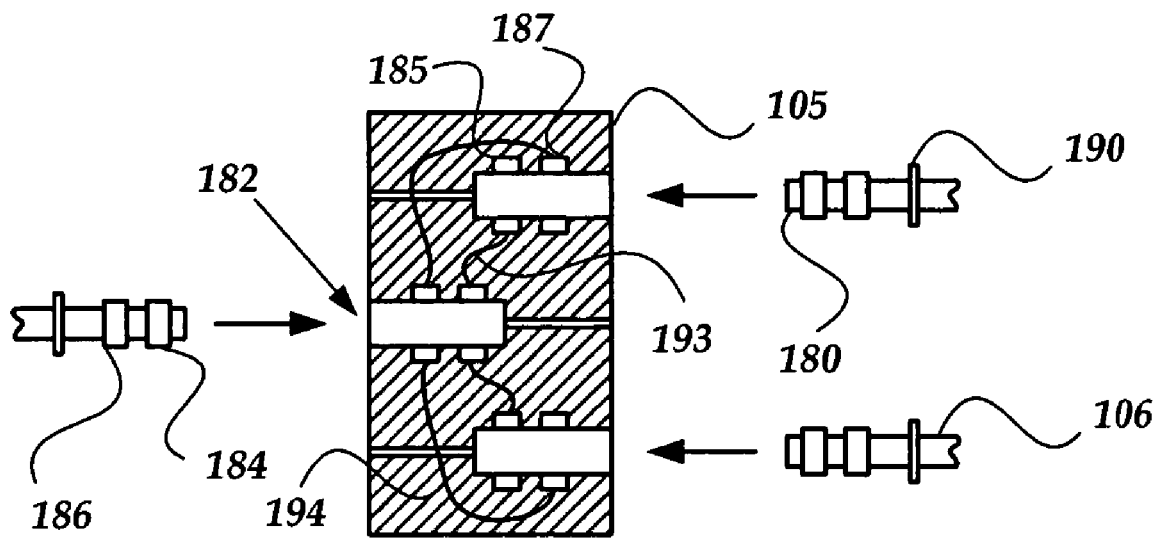
FIG. 9 is a schematic cross-sectional view of another embodiment of a lead connector and leads, according to the invention.

When the lead is non-removably coupled, the conductors 152 of the lead 106 are typically attached to a power source, electronic subassembly, or other component. Examples of removable coupling of a lead 106 to a lead connector 105 are illustrated in FIGS. 8 and 9. The end of the lead 106 can have a male plug 180 with one or more conductive regions 184, 186 that can mate with corresponding conductive region(s) 185, 187 of a female receptacle 182 of the lead connector 105. Conductor(s) 193, 194 within the lead connector 105 connect the corresponding conductive region(s) 185, 187. An optional sealing member 190 can be provided around the lead to facilitate sealing of the receptacle 182 from fluids. Preferably, a hermetic seal is made when the male plug is plugged into the female receptacle. Optionally, the lead connector can include a suture hole that can be used to suture the lead, and optionally the lead connector, in place. It will be recognized that a similar arrangement with a male plug and female receptacle can be provided for removably coupling a lead 106 to a microstimulator unit 102 or battery unit 104. It will also be recognized that a lead could include a female receptacle and the microstimulator unit, battery unit, or lead connector could include a corresponding male plug.

A lead connector 105 can connect two or more leads. For example, lead connectors for connecting three leads, one lead that directly or indirectly comes from the battery unit and two leads that each directly or indirectly proceed to one or more microstimulator units, are illustrated in FIGS. 8 and 9. It will be recognized that lead connectors can be made which allow connection of more than two leads that proceed directly or indirectly to microstimulator units.

The microstimulator arrangement or portions of the microstimulator arrangement can be implanted individually or together into the body tissue using a variety of methods including surgical methods. In some embodiments, portions of the microstimulator arrangement, such as the microstimulator leads, can be implanted using a hypodermic needle or other insertion cannula. Examples of insertion techniques can be found in U.S. Pat. No. 6,051,017.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable microstimulator arrangement, comprising:
   a plurality of implantable microstimulator units, each of the plurality of microstimulator units individually comprising
      a first implantable housing,
      at least two electrodes disposed on, or as part of, the first implantable housing, and
      an electronic subassembly disposed in the first implantable housing and coupled to the at least two electrodes, the electronic subassembly configured and arranged to generate electrical pulses at the at least two electrodes to stimulate adjacent tissue when implanted, the electronic subassembly comprising a processor configured and arranged to control characteristics of the generated electrical pulses;
   an implantable battery unit comprising
      a second implantable housing, and
      a power source disposed in the second implantable housing,
      wherein the implantable battery unit is separate from the plurality of implantable microstimulator units; and
   a plurality of leads coupling the plurality of microstimulator units to the battery unit.

2. The implantable microstimulator arrangement of claim 1, wherein the power source of the implantable battery unit comprises a primary battery.

3. The implantable microstimulator arrangement of claim 1, wherein the power source of the implantable battery unit comprises a rechargeable battery.

4. The implantable microstimulator arrangement of claim 1, wherein the implantable battery unit further comprises a DC/AC converter.

5. The implantable microstimulator arrangement of claim 1, wherein the implantable battery unit further comprises an antenna.

6. The implantable microstimulator arrangement of claim 5, wherein the processor is coupled to a receiver in communication with the antenna.

7. The implantable microstimulator arrangement of claim 1, wherein the implantable microstimulator arrangement comprises at least three implantable microstimulator units, wherein each microstimulator unit is configured and arranged to stimulate the tissue adjacent that microstimulator unit using the electrical pulses generated by the electronic subassembly of that microstimulator unit.

8. The implantable microstimulator arrangement of claim 7, further comprising at least one lead connector disposed between the implantable battery unit and at least one of the implantable microstimulator units and configured and arranged to receive and electrically couple at least two of the plurality of leads to allow electrical signals from one lead to be transmitted to another lead.

9. The implantable microstimulator arrangement of claim 8, wherein the implantable microstimulator arrangement comprises a plurality of lead connectors, wherein each lead connector is configured and arranged to receive and electrically couple at least two of the plurality of leads to allow electrical signals from one lead to be transmitted to another lead.

10. The implantable microstimulator of claim 8, wherein the plurality of leads comprises at least three leads and wherein the at least one lead connector is configured and arranged to receive and electrically couple the at least three leads to allow electrical signals from one lead to be transmitted to another lead.

11. The implantable microstimulator arrangement of claim 1, wherein the implantable microstimulator arrangement comprises a plurality of battery units and a plurality of leads, wherein each of the battery units is coupled to a remainder of the microstimulator arrangement using a different lead.

12. The implantable microstimulator arrangement of claim 1, wherein a one of the plurality of implantable microstimulator units further comprises an antenna disposed in the first implantable housing.

13. The implantable microstimulator arrangement of claim 1, wherein a one of the plurality of leads is removably coupled to the battery unit.

14. The implantable microstimulator arrangement of claim 1, wherein a one of the plurality of leads is removably coupled to a one of the plurality of microstimulator units.

15. The implantable microstimulator arrangement of claim 1, wherein the processor is configured to control timing of the electrical pulse.

16. The implantable microstimulator arrangement of claim 1, wherein the processor is configured to produce a signal to begin charging the battery.

17. An implantable microstimulator arrangement, comprising:
at least one implantable battery unit comprising
a first implantable housing, and
a power source disposed in the first implantable housing;
a plurality of implantable microstimulator units, wherein each implantable microstimulator unit comprises
a second implantable housing,
at least two electrodes disposed on, or as part of, the second implantable housing, and
an electronic subassembly disposed in the second implantable housing and coupled to the at least two electrodes, the electronic subassembly configured and arranged to generate electrical pulses at the at least two electrodes to stimulate adjacent tissue when implanted, the electronic subassembly comprising a processor configured and arranged to control characteristics of the generated electrical pulses;
a plurality of lead connectors; and
a plurality of leads that couple the microstimulator units to the at least one battery unit using the lead connectors
wherein the at least one implantable battery unit is separate from the plurality of implantable microstimulator units.

18. A method of treating body tissue, the method comprising:
implanting at least one microstimulator unit into a body in the proximity of the body tissue to be treated, each microstimulator unit comprising a first housing, at least two electrodes disposed on, or as part of, the first housing, and an electronic subassembly disposed in the first housing and coupled to the at least two electrodes, the electronic subassembly configured and arranged to generate electrical pulses at the at least two electrodes to stimulate the body tissue, the electronic subassembly comprising a processor configured and arranged to control characteristics of the generated electrical pulses;
implanting a separate battery unit into the body, the battery unit comprising a second implantable housing and a power source disposed in the second implantable housing;
coupling the battery unit to the microstimulator unit using at least one lead prior to implanting the at least one microstimulator unit; and
operating the microstimulator unit to treat the body tissue.

19. The method of claim 18, wherein implanting at least one microstimulator unit comprises implanting a plurality of microstimulator units.

20. The method claim 19, wherein implanting a plurality of microstimulator units comprises implanting a plurality of microstimulator units to treat a plurality of body tissue regions.

21. The method of claim 19, wherein coupling the battery unit to the microstimulator unit comprises coupling the battery unit to the plurality of microstimulator units using a plurality of leads and at least one lead connector that receives and electrically couples at least two of the plurality of leads to allow electrical signals from one lead to be transmitted to another lead.

22. The method of claim 15, further comprising replacing the battery unit without removing the at least one microstimulator unit.

* * * * *